United States Patent
Liu et al.

(10) Patent No.: US 7,381,317 B2
(45) Date of Patent: Jun. 3, 2008

(54) METHODS AND COMPOSITIONS FOR CAPILLARY ELECTROPHORESIS (CE)

(75) Inventors: Yu Liu, Diamond Bar, CA (US); M. Parameswara Reddy, Brea, CA (US); Chitra K. Ratnayake, Yorba Linda, CA (US); Edward V. Koh, Diamond Bar, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 822 days.

(21) Appl. No.: 10/607,584

(22) Filed: Jun. 27, 2003
(Under 37 CFR 1.47)

(65) Prior Publication Data

US 2004/0050702 A1    Mar. 18, 2004

Related U.S. Application Data

(60) Provisional application No. 60/402,684, filed on Aug. 12, 2002.

(51) Int. Cl.
*G01N 27/453* (2006.01)
(52) U.S. Cl. ........................ 204/605; 204/455
(58) Field of Classification Search ................ 204/605, 204/455, 601, 451, 602–604, 452–454
See application file for complete search history.

(56) References Cited

U.S. PATENT DOCUMENTS 3,622,661 A * 11/1971 King et al. ................... 424/50

| | | | |
|---|---|---|---|
| 4,522,742 A | 6/1985 | Lee et al. | 252/301.16 |
| 4,865,706 A | 9/1989 | Karger et al. | 204/182.8 |
| 5,015,350 A | 5/1991 | Wiktorowicz | 204/180.1 |
| 5,089,111 A | 2/1992 | Zhu et al. | 204/180.1 |
| 5,112,460 A | 5/1992 | Karger et al. | 204/182.8 |
| 5,120,413 A | 6/1992 | Chen et al. | 204/180.1 |
| 5,139,630 A | 8/1992 | Chen | 204/180.1 |
| 5,213,669 A * | 5/1993 | Guttman | 204/452 |
| 5,259,939 A | 11/1993 | Chen | 204/180.1 |
| 5,264,101 A | 11/1993 | Demorest et al. | 204/299 |
| 5,292,372 A | 3/1994 | Swaisgood et al. | 134/1 |
| 5,292,416 A | 3/1994 | Novotny et al. | 204/182.8 |
| 5,310,462 A | 5/1994 | Chen | 204/180.1 |
| 5,332,481 A | 7/1994 | Guttman | 204/182.8 |
| 5,364,520 A | 11/1994 | Okuyama et al. | 204/299 |
| 5,370,777 A | 12/1994 | Guttman et al. | 204/182.8 |
| 5,374,527 A | 12/1994 | Grossman | 435/6 |
| 5,384,024 A | 1/1995 | Moring et al. | 204/299 |
| 5,421,980 A | 6/1995 | Guttman | 204/299 |
| 5,423,966 A | 6/1995 | Wiktorowicz | 204/182.8 |
| 5,490,909 A | 2/1996 | Wang et al. | 204/452 |
| 5,503,722 A | 4/1996 | Guttman | 204/450 |

(Continued)

OTHER PUBLICATIONS

"Dextran Product Information" Sigma-Aldrich (2001) found at http://www.sigmaaldrich.com/sigma-aldrich/product_information_sheet/d5376pis.pdf.*

(Continued)

*Primary Examiner*—Kaj K Olsen
(74) *Attorney, Agent, or Firm*—Townsend and Townsend and Crew

(57) ABSTRACT

This invention relates to improved methods and compositions for conducting Capillary Electrophoresis (CE) to separate molecules on the basis of their respective size or charge.

48 Claims, 12 Drawing Sheets

Separation of Reduced IgG Using Dextran Gel in Different Buffer Systems

U.S. PATENT DOCUMENTS

| | | | |
|---|---|---|---|
| 5,514,543 A | 5/1996 | Grossman et al. | 435/6 |
| 5,534,123 A | 7/1996 | Bashkin et al. | 204/455 |
| 5,545,302 A | 8/1996 | Zhu et al. | 204/454 |
| 5,552,028 A | 9/1996 | Madabhushi et al. | 204/451 |
| 5,567,292 A | 10/1996 | Madabhushi et al. | 204/451 |
| 5,580,016 A | 12/1996 | Sarine | 248/188.2 |
| 5,582,705 A | 12/1996 | Yeung et al. | 204/603 |
| 5,665,216 A | 9/1997 | Karger et al. | 204/605 |
| 5,695,626 A | 12/1997 | Yeung et al. | 204/605 |
| 5,728,282 A | 3/1998 | Bashkin et al. | 204/455 |
| 5,741,411 A | 4/1998 | Yeung et al. | 204/452 |
| 5,777,096 A | 7/1998 | Grossman et al. | 536/24.3 |
| 5,840,388 A | 11/1998 | Karger et al. | 428/36.91 |
| 5,846,395 A | 12/1998 | Sarrine et al. | 204/464 |
| 5,891,313 A | 4/1999 | Johnson et al. | 204/451 |
| 5,916,426 A | 6/1999 | Madabhushi et al. | 204/451 |
| 5,948,227 A | 9/1999 | Dubrow | 204/455 |
| 5,958,694 A | 9/1999 | Nikiforov | 435/6 |
| 5,964,995 A | 10/1999 | Nikiforov et al. | 204/450 |
| 5,976,336 A | 11/1999 | Dubrow et al. | 204/453 |
| 5,989,399 A | 11/1999 | Chu et al. | 204/456 |
| 6,001,232 A | 12/1999 | Chu et al. | 204/455 |
| 6,033,546 A | 3/2000 | Ramsey | 204/603 |
| 6,042,710 A | 3/2000 | Dubrow | 204/454 |
| 6,068,752 A | 5/2000 | Dubrow et al. | 204/604 |
| 6,074,542 A | 6/2000 | Dolnik et al. | 204/454 |
| 6,107,044 A | 8/2000 | Nikiforov et al. | 435/6 |
| 6,129,826 A | 10/2000 | Nikiforov et al. | 204/450 |
| 6,153,073 A | 11/2000 | Dubrow et al. | 204/453 |
| 6,235,175 B1 | 5/2001 | Dubrow et al. | 204/453 |
| 6,274,089 B1 | 8/2001 | Chow et al. | 422/101 |
| 6,306,273 B1 | 10/2001 | Wainwright et al. | 204/454 |
| 6,316,201 B1 | 11/2001 | Nikiforov | 435/6 |
| RE37,606 E | 3/2002 | Guttman | 204/455 |
| 6,355,709 B1 | 3/2002 | Madabhushi et al. | 524/104 |
| 6,358,385 B1 | 3/2002 | Madabhushi et al. | 204/451 |
| 6,372,353 B2 | 4/2002 | Karger et al. | 428/447 |
| 6,410,668 B1 | 6/2002 | Chiari | 526/238.23 |
| 6,423,296 B1 | 7/2002 | Gunther et al. | 424/9.322 |
| 6,436,646 B1 | 8/2002 | Nikiforov et al. | 435/6 |
| 6,440,284 B1 | 8/2002 | Dubrow | 204/455 |
| 6,787,016 B2 * | 9/2004 | Tan et al. | 204/455 |

OTHER PUBLICATIONS

"Dextran Sulfate Product Information" Sigma-Aldrich (2001) found at http://www.sigmaaldrich.com/sigma/product%20information%20sheet/d8906pis.pdf.*

Bean, et al. *Sodium Dodecyl Sulfate Capillary Electrophoresis of Wheat Proteins. 1. Uncoated Capillaries* J. Agric. Food Chem., vol. 47, No. 10, 1999 p. 4246-4255.

Sanders, et al. *Neutral and Deae Dextrans as Tracers for Assessing Lung Microvascular Barrier Permeability and Integrity* j. Appl. Physiol. vol. 93, Jul. 2002 pp.251-262.

Bean, S.R. et al. (1999) ("Sodium Dodecyl Sulfate Capillary Electrophoresis of Wheat Proteins. 1. Uncoated Capillaries," J. Agric. Food Chem 47(10):4246-4255.

Ganzler, K. et al. (1992) "High-Performance Capillary Electrophoresis of SDS-Protein Complexes Using UV-Transparent Polymer Networks," Anal. Chem. 64:2665-2671.

Hjerten, S. et al. (1989) "High-Performance Electrophoresis of Acidic and Basic Low-Molecular-Weight Compounds and Proteins in the Presence of Polymers and Neutral Surfactants," J. Liquid Chromatog. 12:2471-2499.

Doln_ik, (2003) "Sieving Matrices in Capillary Electrophoresis," http://neo.pharm.hiroshima-u.ac.jp/ccab/2nd/mini_review/mr130/dolnik.html.

Donald, A. "Gels and Networks," (2003) http://www.poco.phy.cam.ac.uk/teaching/A_Donald/Gels_and_Network.htm.

Kemp, G. (1998) "Capillary Electrophoresis: A Versatile Family of Analytical Techniques," Biotechnol. Appl. Biochem. 27:9-17.

Lausch, R. et al. (1993) "Rapid Capillary Gel Electrophoresis of Proteins," J. Chromatogr. 654:190-195.

Manabe, T. et al. (1998) "Size Separation of Sodium Dodecyl Sulfate Complexes of Human Plasma Proteins by Capillary Electrophoresis Employing Linear Polyacrylamide as a Sieving Polymer," Electrophoresis 19:2308-16.

Wu, D. et al. (1992) ("Sodium Dodecyl Sulfate-Capillary Gel Electrophoresis of Proteins Using Non-Cross-Linked Polyacrylamide," J. Chromatogr. 608:349-356.

Zhang, Y. et al. (1996) "Separation of Myoglobin Molecular Mass Markers Using Non-Gel Sieving Capillary Electrophoresis," J. Chromatog. A 744:249-257.

* cited by examiner

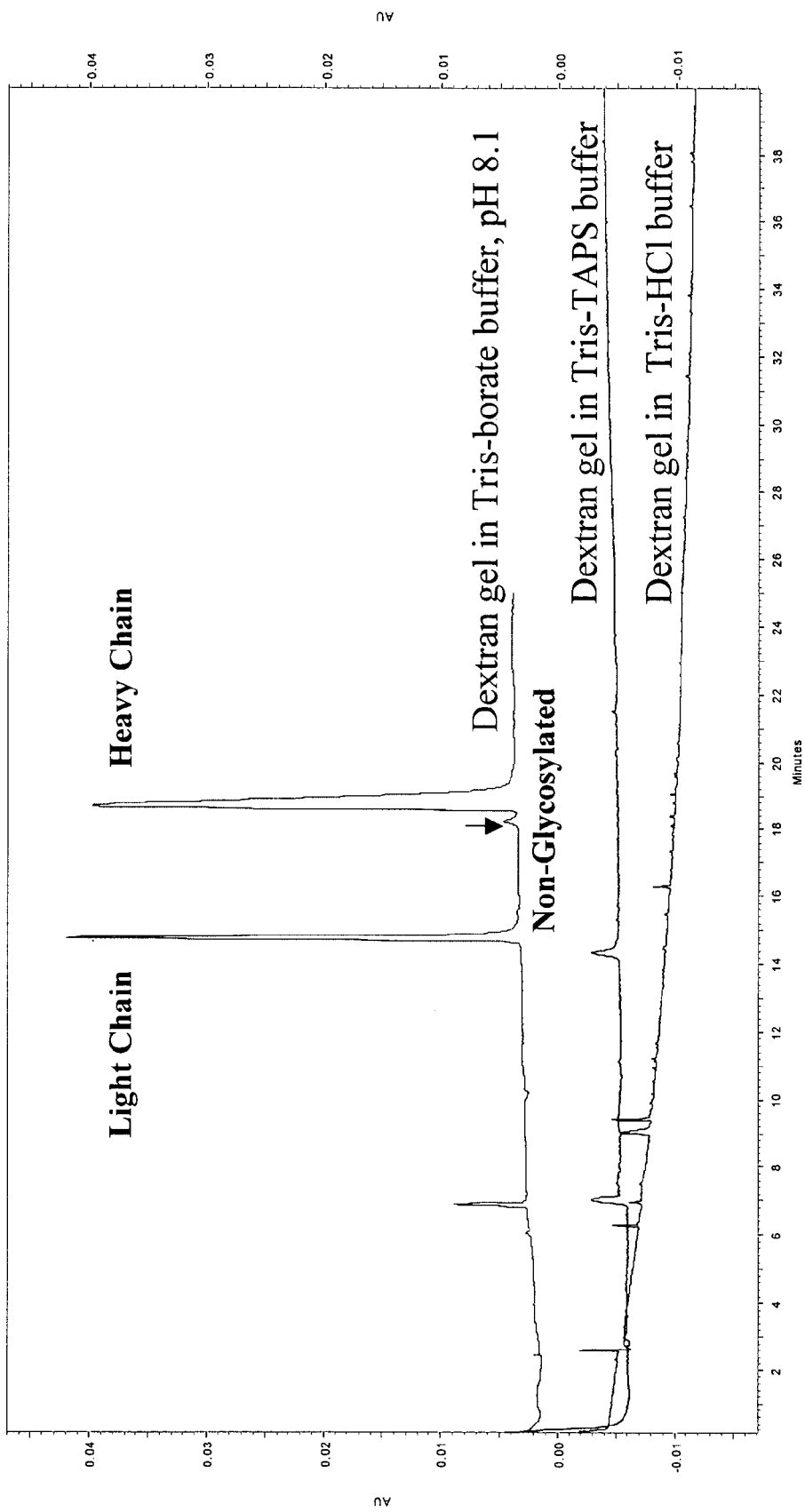
Figure 2  Separation of Reduced IgG Using Dextran Gel in Different Buffer Systems

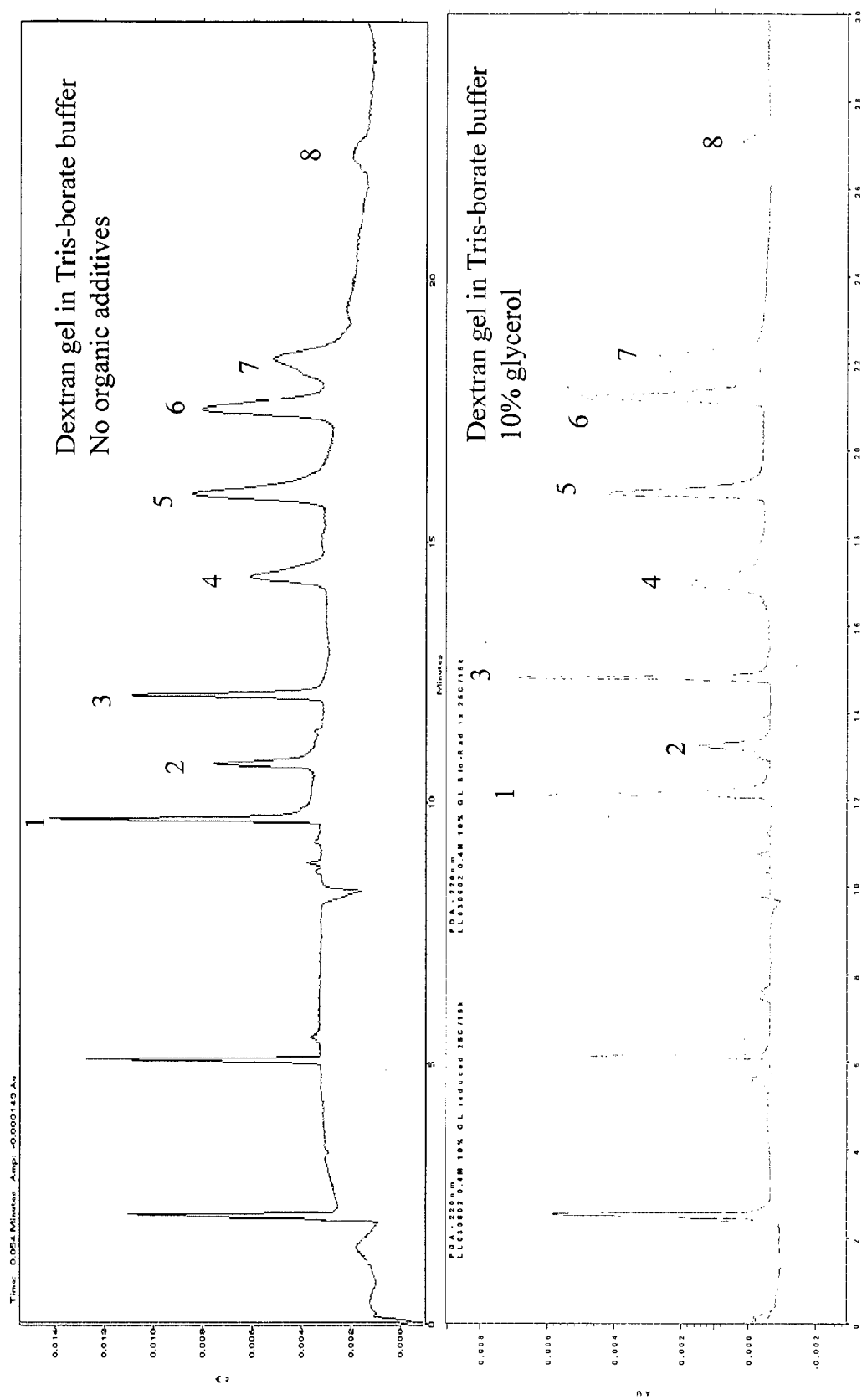
Figure 3  Enhanced separation of broad range protein with organic additives

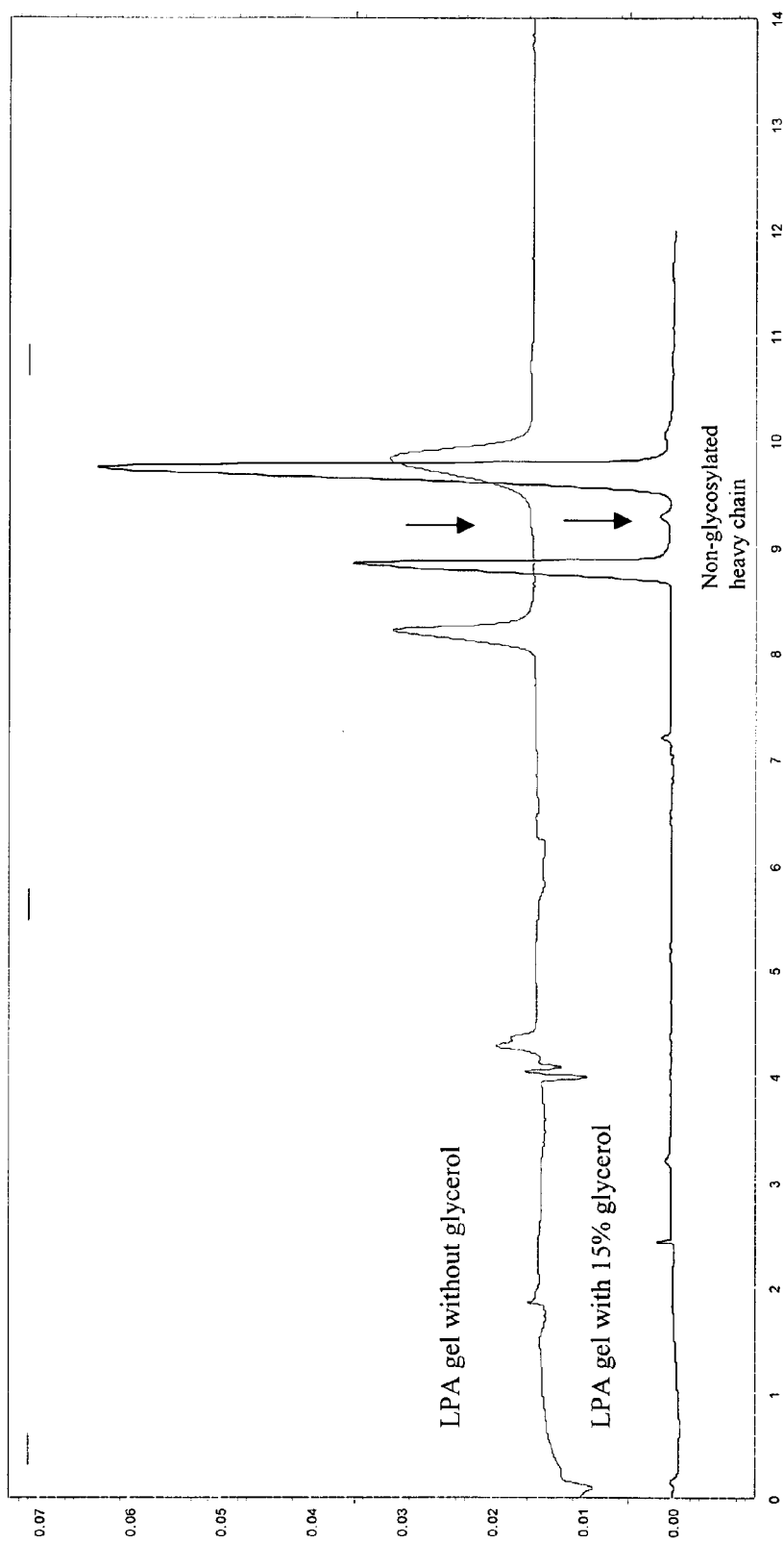
Figure 4  Separation of reduced Human IgG-SDS complex on LPA

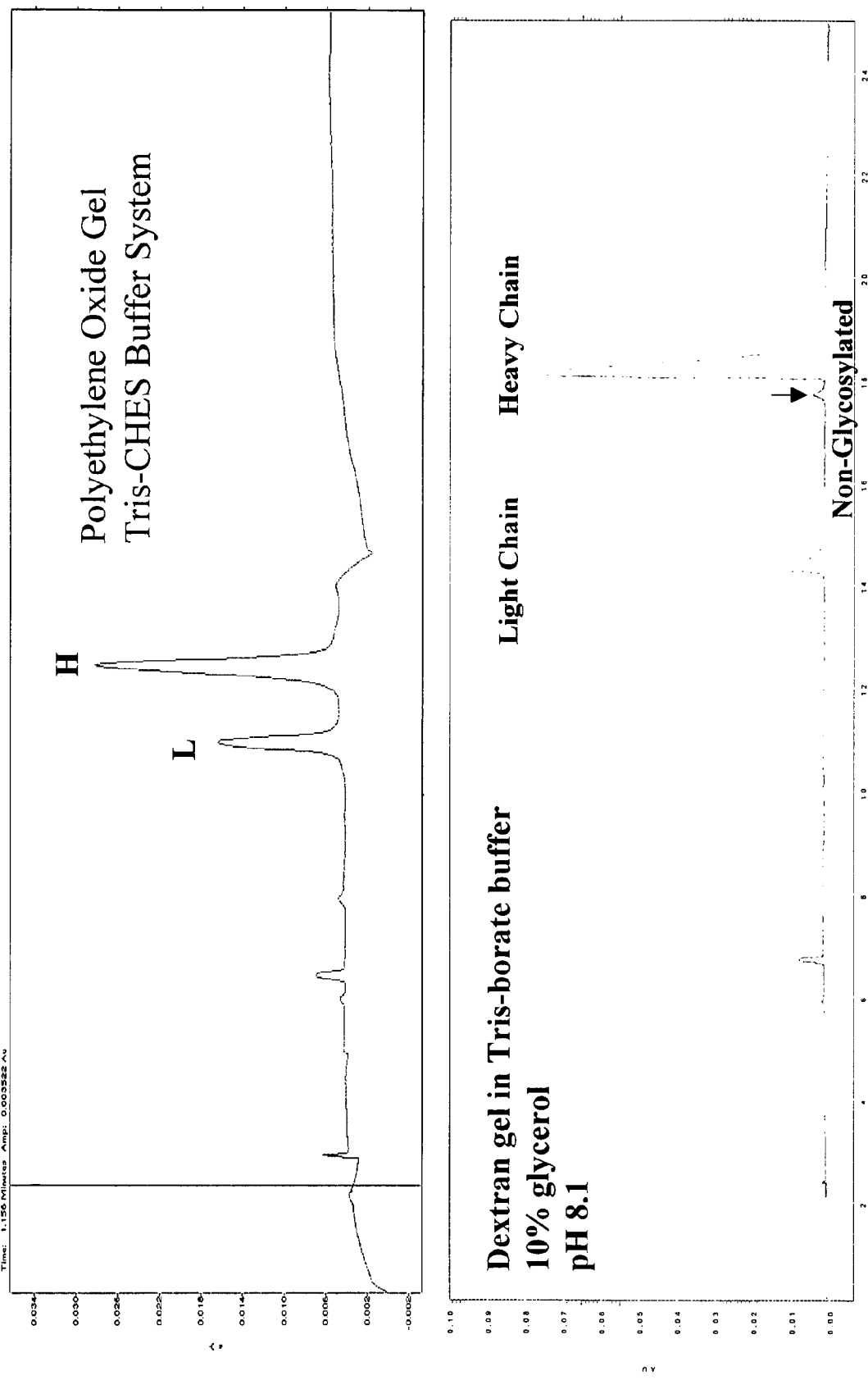
Figure 5  Separation of SDS complex of reduced human IgG

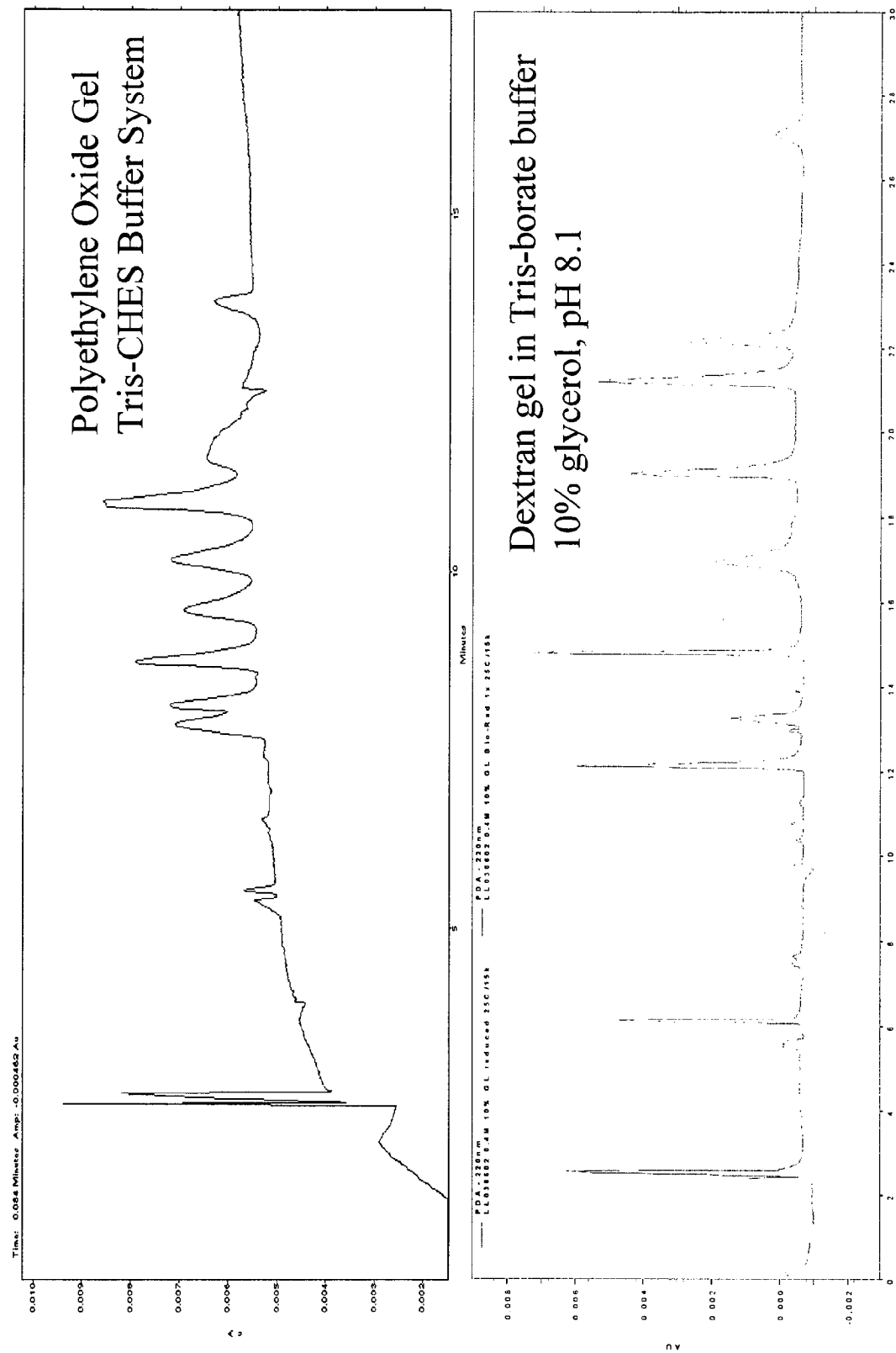
Figure 6 Separation of SDS protein size standard (14 to 200 kD)

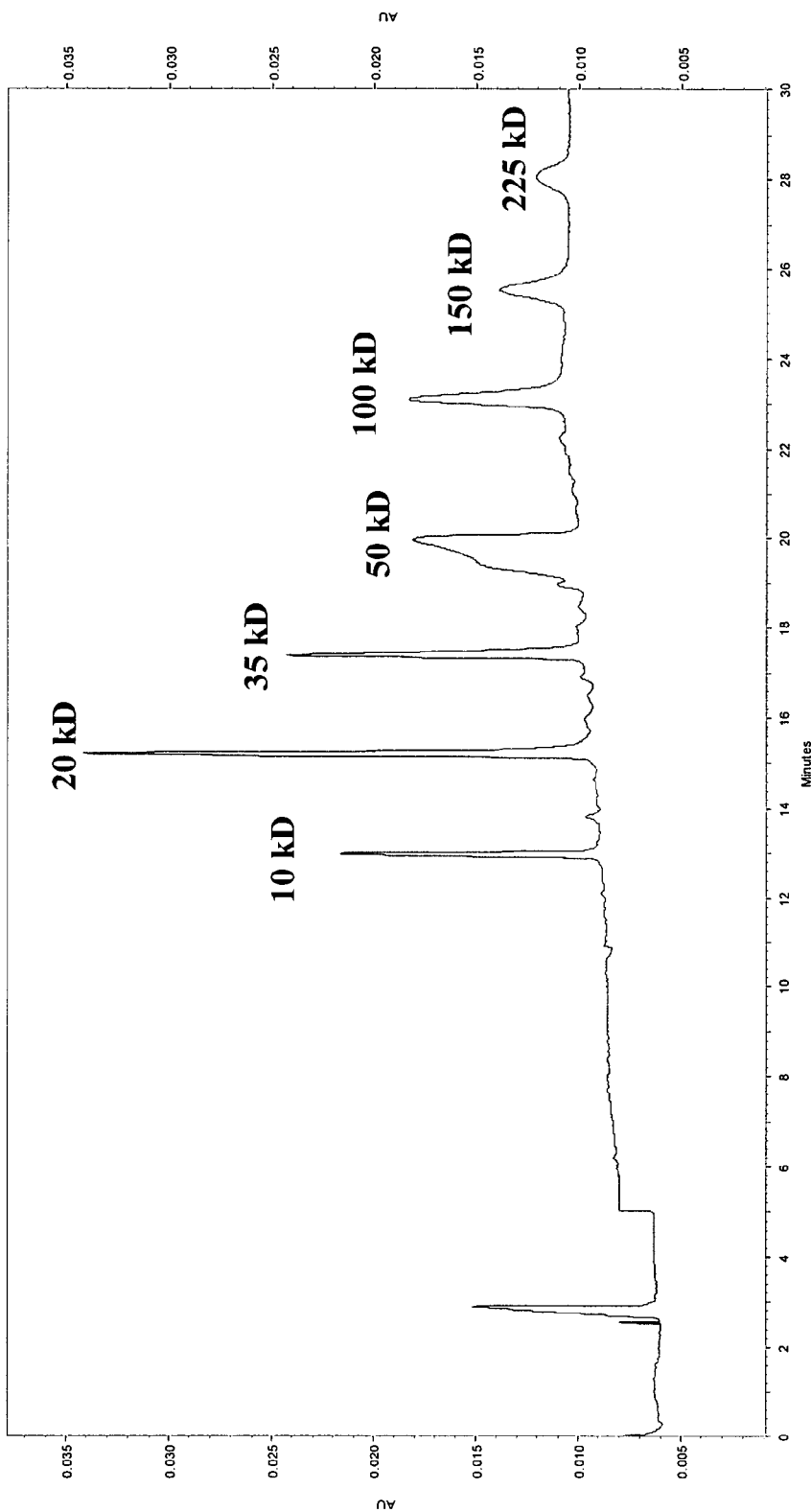
Figure 7 Separation of MW Size Standard Using SDS gel Prepared New Dextran Lot

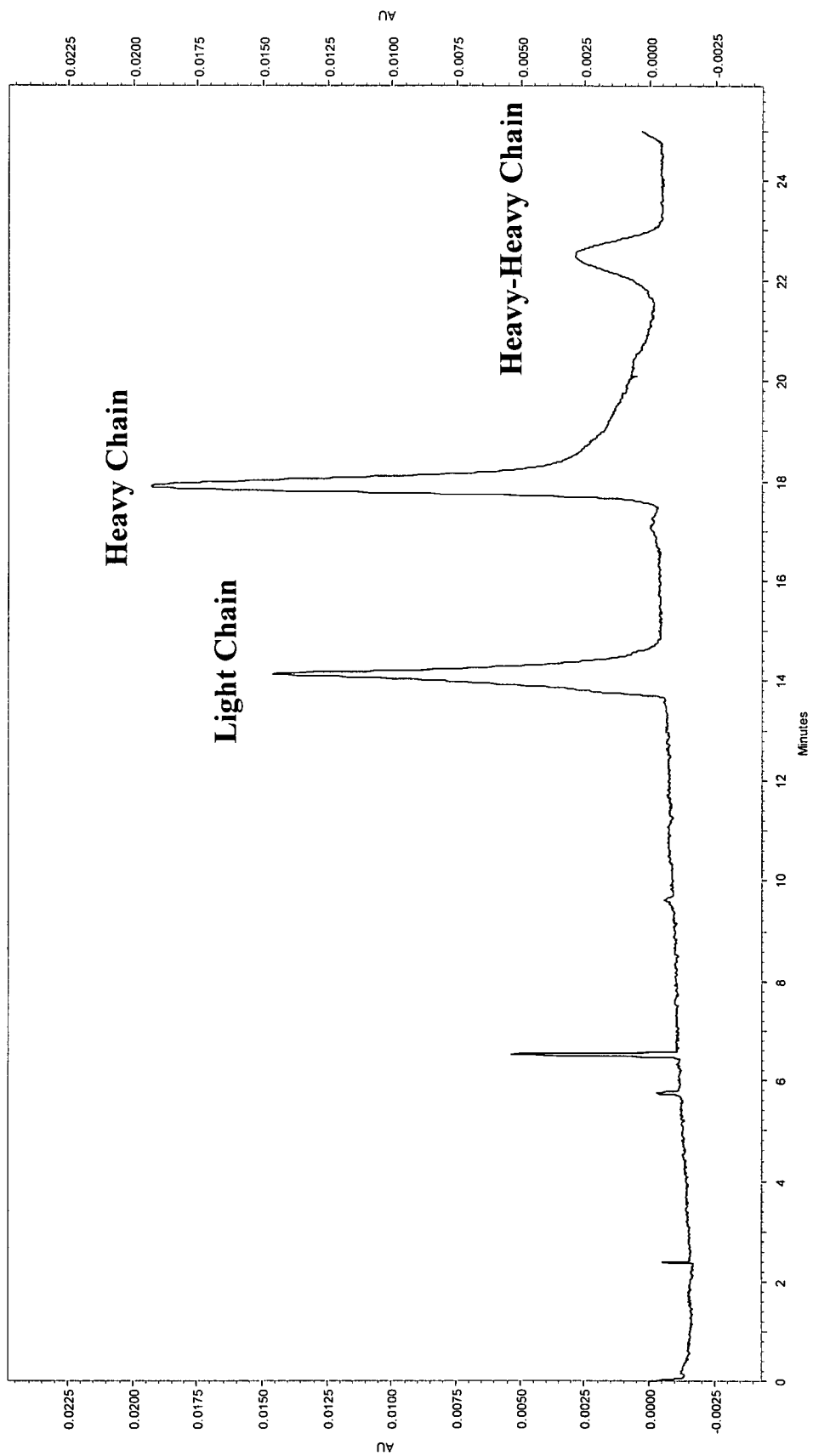
Figure 8 Separation of Reduced IgG Using SDS gel Prepared New Dextran Lot

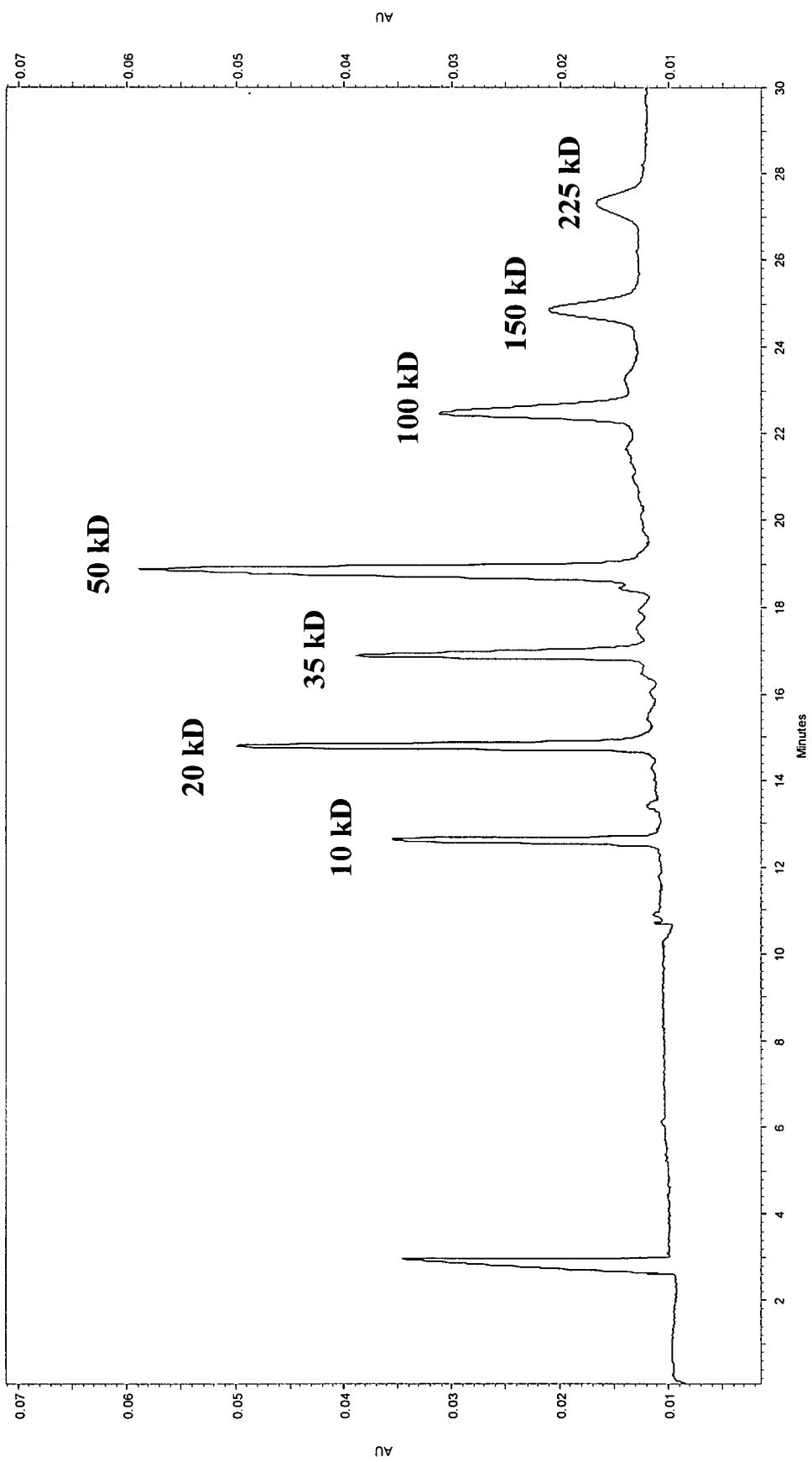
Figure 9 Separation of MW Size Standard Using SDS gel with 1 mM DTT

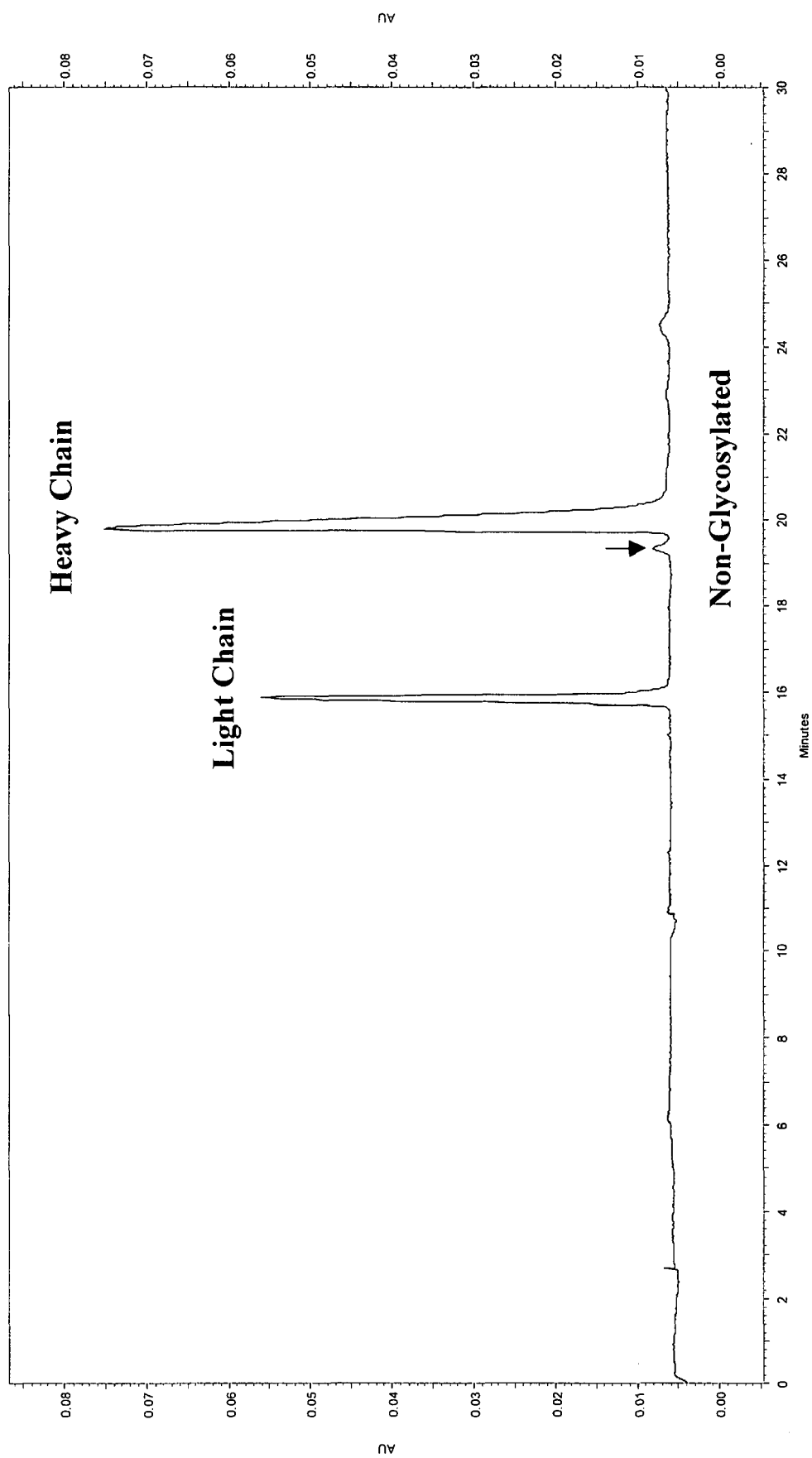
Figure 10 Separation of Reduced IgG Using SDS Gel with 1 mM DTT

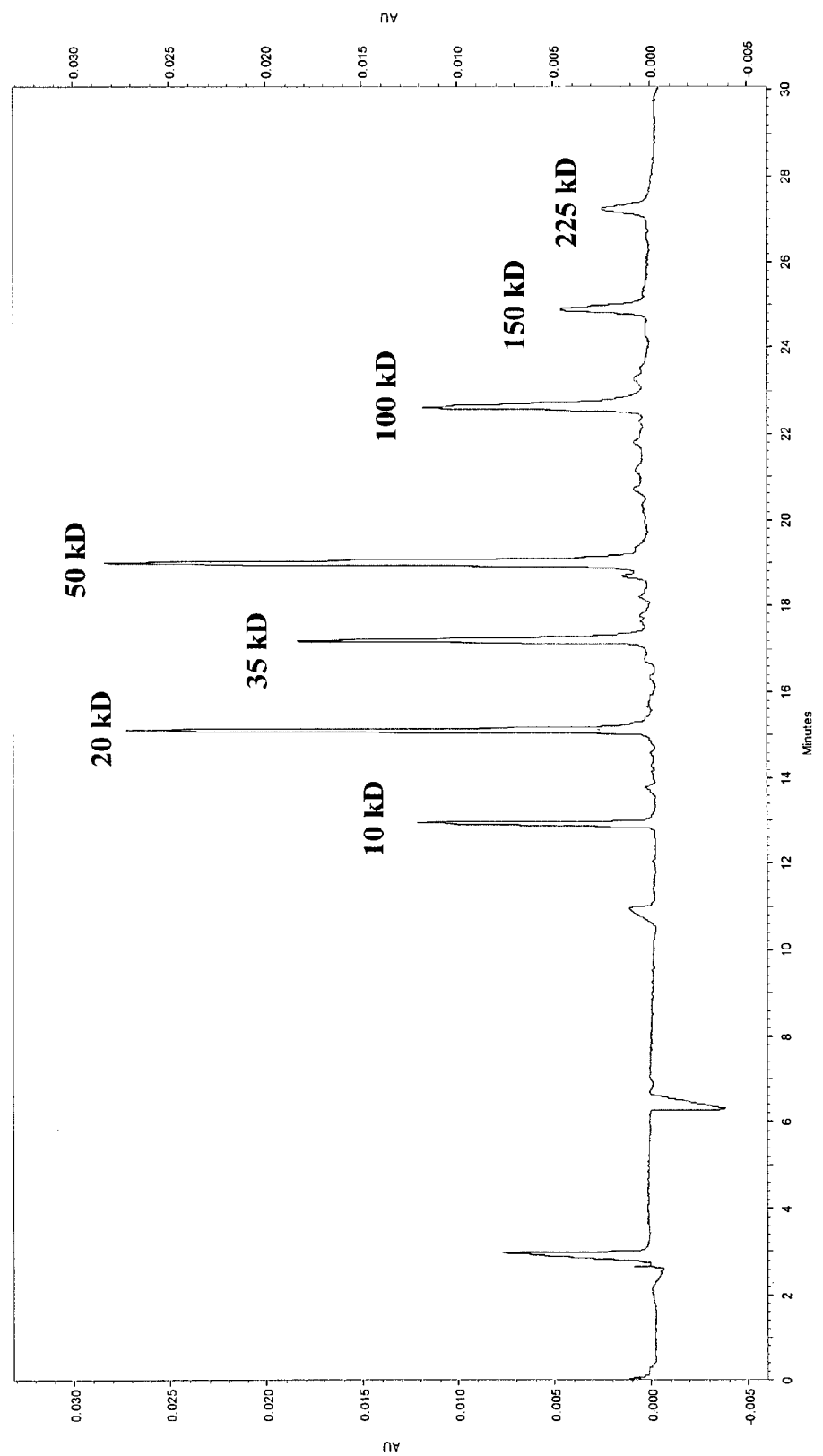
Figure 11 Separation of MW Size Standard Using SDS gel with 5 mM EDTA

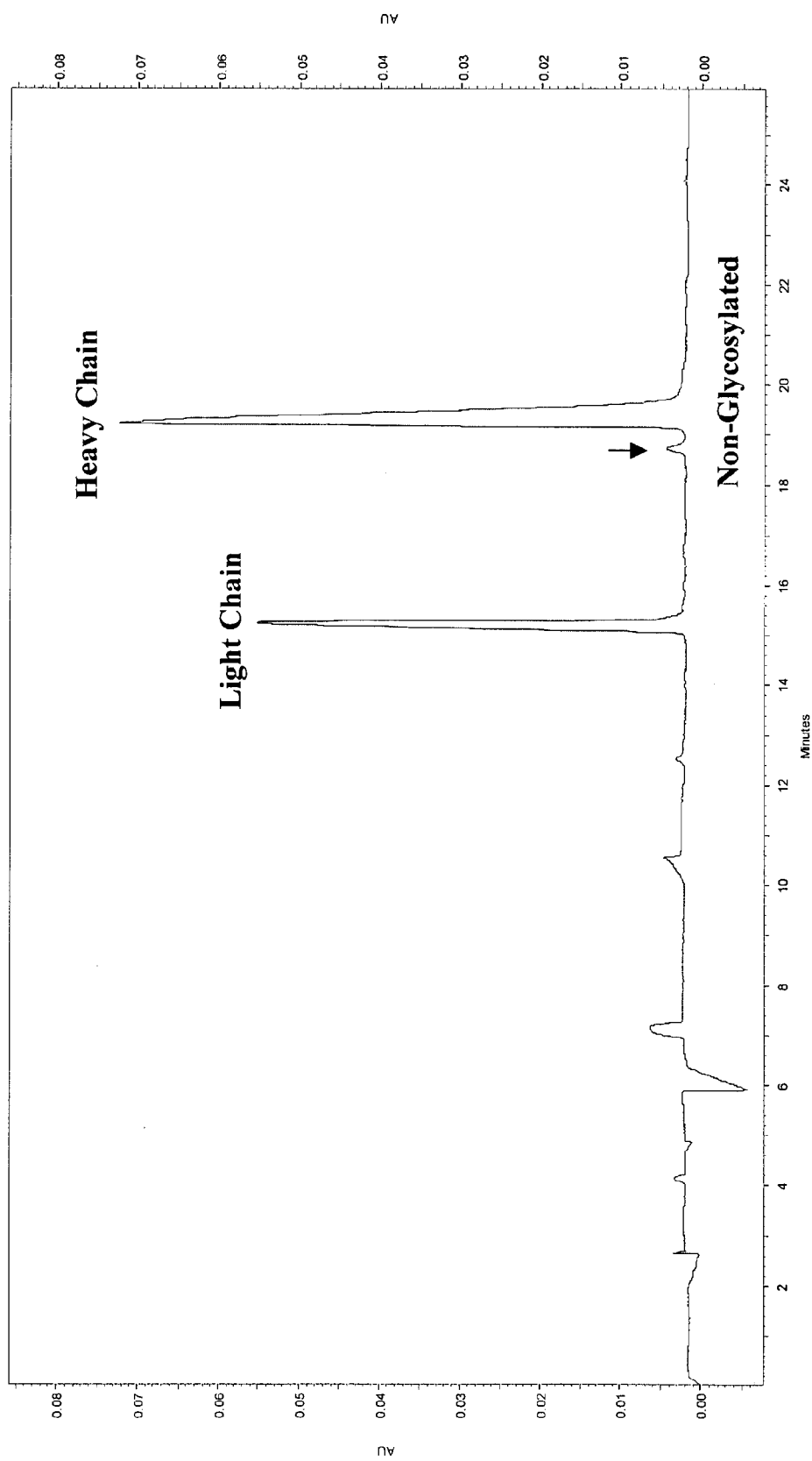
Figure 12 Separation of Reduced IgG Using SDS Gel with 5 mM EDTA

METHODS AND COMPOSITIONS FOR CAPILLARY ELECTROPHORESIS (CE)

CROSS-REFERENCE TO RELATED APPLICATIONS

This application claims priority to U.S. Patent Application Ser. No. 60/402,684, filed on Aug. 12, 2002, herein incorporated by reference in its entirety.

FIELD OF THE INVENTION

This invention relates to improved methods and compositions for conducting Capillary Electrophoresis (CE) to separate molecules on the basis of their respective size or charge.

BACKGROUND OF THE INVENTION

There is a growing need for analysis of biomolecules, including proteins, polypeptides and DNA. Capillary electrophoresis (CE) is a process for separating molecules based on their size or charge. In capillary electrophoresis molecules are introduced into a fluid-filled capillary tube and subjected to an electric field (see, Kemp, G. (1998) "CAPILLARY ELECTROPHORESIS: A VERSATILE FAMILY OF ANALYTICAL TECHNIQUES," Biotechnol. Appl. Biochem. 27:9-17; Wu, D. et al. (1992). Capillary electrophoresis techniques are reviewed by Schwartz, H. et al. ("Separation of Proteins and Peptides by Capillary Electrophoresis: Application to Analytical Biotechnology," http://www.beckman.com/Literature/BioResearch/727484.pdf), Capillary electrophoresis (CE) has become an attractive alternative to traditional slab gel electrophoresis for biomolecular separations due to its fast speed and high efficiency. Two primary separation mechanisms are commonly used in CE, separations based on differences in the effective charge of analytes, and separations based on their molecular size. The first separation mechanism is limited to small molecules. Many biomolecules, such as large proteins and DNA are generally separated by molecular sieving electrophoresis and such separations are typically carried out using gel matrices of controlled pore sizes. This technique is also referred as "capillary gel electrophoresis" ("CGE"). The separation achieved using CGE results from the differences in the abilities of different sized molecule to penetrate the gel matrix. Since small molecules move faster than large molecules through the separation gel, size separation is achieved. As for polypeptides and proteins, it is necessary to denature the material (for example, with a sodium dodecyl sulfate (SDS) buffer solution), so that all the proteins will have the same effective charges.

As molecules increase in size the relative differences in their charge diminish. Thus, for larger molecules, such as proteins or nucleic acid molecules, CE is implemented in a manner that accomplishes separation based on size rather than molecular charge. Such size separation is generally accomplished using molecular sieving electrophoresis in which the molecules are drawn through a gel matrix of controlled pore size. It is generally necessary to denature proteins and polypeptides with detergents (e.g., sodium dodecyl sulfate (SDS)), so that disparities in effective charge will not distort the rate with which molecules migrate through the matrix. The process is known as "capillary gel electrophoresis" ("CGE").

Numerous approaches for accomplishing capillary electrophoresis have been previously described (see, for example, U.S. Pat. Nos.: RE37,606; 6,440,284; 6,436,646; 6,410,668; 6,372,353; 6,358,385; 6,355,709; 6,316,201; 6,306,273; 6,274,089; 6,235,175; 6,153,073; 6,129,826; 6,107,044; 6,074,542; 6,068,752; 6,042,710; 6,033,546; 6,001,232; 5,989,399; 5,976,336; 5,964,995; 5,958,694; 5,948,227; 5,916,426; 5,891,313; 5,846,395; 5,840,388; 5,777,096; 5,741,411; 5,728,282; 5,695,626; 5,665,216; 5,582,705; 5,580,016; 5,567,292; 5,552,028; 5,545,302; 5,534,123; 5,514,543; 5,503,722; 5,423,966; 5,421,980; 5,384,024; 5,374,527; 5,370,777; 5,364,520; 5,332,481; 5,310,462; 5,292,416; 5,292,372; 5,264,101; 5,259,939; 5,139,630; 5,120,413; 5,112,460; 5,015,350; 4,865,706).

U.S. Pat. No. 5,089,111 (Zhu et al.) and U.S. Pat. No. 5,545,302 (Zhu et al.), for example, concern gel-free approaches to capillary electrophoresis. U.S. Pat. No. 5,089,111 (Zhu et al.) discloses an electrophoretic method of separating a mixture of sample ions of varying molecular weights in a sample into components in which the sample is passed through a separation column containing a gel-free aqueous solution of a water-soluble polymer selected from the group consisting of cellulose derivatives, saccharide-based and substituted saccharide-based polymers, polysilanes, polyvinylalcohol and polyvinylpyrrolidone, and in which the polymer has a molecular weight of about 10,000 to about 2,000,000, and is within a range of about 0.1 to about 200 times the average molecular weight of the sample ions in the mixture. The concentration of the polymer in adjusted so as to be sufficient to retard the flow of the species through the separation column to degrees which vary with their molecular weights. The a gel-free aqueous polymer method of U.S. Pat. No. 5,089,111 (Zhu et al.) thus determines the molecular weight of the analytes being separated by retarding the flow of analytes in proportion to their molecular weights. U.S. Pat. No. 5,545,302 (Zhu et al.) concerns a gel-free composition that employs amines to derivative a hydrophilic polymer as a means for reducing endoosmotic flow. The disclosed method concerns suppressing electroendosmotic flow in an electrophoretic separation of a mixture of sample ions in a separation medium consisting essentially of a gel-free aqueous solution, the method comprising including in the gel-free aqueous solution a hydrophilic polymer derivatized by the bonding thereto of an amine at about 0.05 or more equivalents of amine per 100 grams of the polymer. The patent discloses mixing derivatized chains and non-derivatized chains are together.

U.S. Pat. No. 5,264,101 (Demorest et al.) discloses a method of separating biomolecules in a sample comprising preparing a capillary tube with two ends, where the capillary tube (i) has charged chemical groups on its inner wall surface, and (ii) is filled with an electrolyte solution containing 0.05 to 30% weight to weight (w/w) of a non-cross-linked, hydrophilic polymer or copolymer solution containing at least one polymer or copolymer species having (a) a molecular weight between 20 and 5,000 kilodaltons, and (b) a percent charge of between 0.01 to 1.0% as measured by the molar percent of charged monomer subunits to the total polymer subunits, where the charged monomer subunits have the charge opposite to the wall charge at a selected electrophoresis pH, immersing the ends of the tube in anodic and cathodic reservoirs containing an electrolyte solution, introducing a sample containing the biomolecules to be separated into one end of the tube, and applying an electric field across the reservoirs with a polarity effective to fractionate the biomolecules in the sample. The polymers taught by U.S. Pat. No. 5,264,101 (Demorest et al.) are highly ionizable (i.e., they must exhibit a percent charge of between 0.01 to 1.0%) polymers such as amino-acrylamides.

One difficulty encountered in the art is undesirable electroendoosmotic flow and analyte-wall interactions. U.S. Pat. No. 5,567,292 (Madabhushi et al.) discloses a method of suppressing electroendoosmotic flow and analyte-wall interactions to facilitate capillary electrophoresis through the use of water-soluble silica-adsorbing polymers. The disclosed method comprises providing a separation medium containing one or more uncharged water-soluble silica-adsorbing polymers having (i) water solubility in a temperature range between about 20° C. and about 50° C., (ii) a concentration in the separation medium in a range between about 0.001% and about 10% weight/volume, (iii) a molecular weight in the range between about $5 \times 10^3$ and about $1 \times 10^6$ 6 daltons, (iv) an absence of charged groups in an aqueous medium having a pH in the range between about 6 and about 9; and employing a separation medium having a viscosity of less than about 1000 centipoise. U.S. Pat. No. 6,358,385 (Madabhushi et al.) concerns a capillary electrophoresis element comprising: a capillary containing an electrophoretic separation medium including a surface interaction component comprising a solution of one or more uncharged water-soluble silica-adsorbing polymers; wherein the inside surface of the capillary is uncoated, and wherein the capillary does not contain a crosslinked polymer gel.

One approach to performing capillary electrophoresis employs charged polymers. U.S. Pat. No. 5,948,227 (Dubrow) concerns a method of separating macromolecules by capillary electrophoresis, comprising: providing a substrate comprising at least a first capillary channel disposed therein, a surface of the channel having a first surface charge associated therewith; filling the capillary channel with a water soluble hydrophilic polymer solution having a percent charge of from about 0.01% to about 2%, as calculated by the molar percent of charged monomer subunits to total monomer utilized in producing the polymer, the charged monomer subunits consist of monomer subunits having a charge that is the same as the first surface charge; introducing a sample containing the macromolecules into one end of the capillary channel and; applying a voltage gradient across the length of the capillary channel, whereby the macromolecules in the sample are separated in the capillary channel. The patent also discusses the use of silica-adsorbing polymers in capillary electrophoresis. U.S. Pat. No. 6,042,710 (Dubrow) discloses a method of manufacturing a microfabricated channel system, the method comprising: providing a device comprising at least one microchannel; and, disposing a polymer in the at least one microchannel, the polymer comprising a net charge of between about 0.01% and 2%, the net charge being of the same charge as at least one surface of the microchannel.

Another means for suppressing undesired analyte-wall interactions invoices the use of coatings to alter the polymer-wall interface. U.S. Pat. No. 5,665,216 (Karger et al.), for example, concerns a coated capillary column containing a UV-transparent polymer network for high performance electrophoretic separation and high sensitivity detection of SDS-proteins comprising: a capillary having an interior cavity and a wall with an inner surface; a layer of coating material on the inner surface of the wall; a UV-transparent hydrophilic polymer network filling the interior cavity; and a UV-transparent buffer, the buffer being selected from a group consisting of Tris-CHES, MES-Na, and AMPD-cacodylic acid (CACO).

Bean, S. R. et al. (1999) ("SODIUM DODECYL SULFATE CAPILLARY ELECTROPHORESIS OF WHEAT PROTEINS. 1. UNCOATED CAPILLARIES," J. Agric. Food Chem 47(10):4246-55) describes the use of high molecular weight non-cross-linked dextran polymers in a capillary electrophoresis system employing SDS and Tris-borate buffers (pH=8.5). The reference describes the ability of organic additives (e.g., ethylene glycol) to improve the composition's ability to separate proteins. Wu, D. et al. (1992) ("SODIUM DODECYL SULFATE-CAPILLARY GEL ELECTROPHORESIS OF PROTEINS USING NON-CROSS-LINKED POLYACRYLAMIDE," J. Chromatogr. 608:349-356) discusses the use of non-crosslinked polyacrylamide in uncoated capillary electrophoresis systems, buffered with a Tris-borate buffer. Lausch, R. et al. (1993) ("RAPID CAPILLARY GEL ELECTROPHORESIS OF PROTEINS," J. Chromatogr. 654:190-195) discusses the use of $2 \times 10^6$ MW dextran in capillary gel electrophoresis in a Tris-CHES buffer system. Manabe, T. et al. (1998) ("SIZE SEPARATION OF SODIUM DODECYL SULFATE COMPLEXES OF HUMAN PLASMA PROTEINS BY CAPILLARY ELECTROPHORESIS EMPLOYING LINEAR POLYACRYLAMIDE AS A SIEVING POLYMER," Electrophoresis 19:2308-16) discusses the use of linear polyacrylamide in capillary gel electrophoresis. Ganzler, K. et al. (1992) ("High-Performance Capillary Electrophoresis of SDS-Protein Complexes Using UV-Transparent Polymer Networks," Anal. Chem. 64:2665-2671) discusses the use of dextran ($2 \times 10^6$ MW) and non-crosslinked polyacrylamide in capillary electrophoresis with UV transparent buffers (AMPD-CACO or Tris-CHES).

Unfortunately, two main problems limit the use of CGE. First, only certain polymers are capable of separating polynucleotides and proteins, and many bind only poorly to the capillary surface. Thus, separations are marred by undesired capillary surface electroosmotic flow and surface absorptions. For example, one difficulty encountered in the use of cellulose derivatives in CGE involves the need to suppress capillary surface electroosmotic flow. Prior-employed PEG and dextrans cannot sufficiently suppress capillary surface electroosmotic flow, so acidic pH (pH 2.5) must be applied in order to reduce electroosmotic flow and surface absorptions. Second, glass, commonly used as the capillary material, possess silanol groups that will ionize in water at pH>3. The dissociation of the silanol groups generates a negative charge on the inner surface of the capillary and promotes undesired electroosmotic flow, wall adsorption and peak tailing.

Thus, despite all prior efforts, a need remains to identify polymer compositions that would facilitate improved capillary electrophoretic separations of biomolecules, and in particular, would facilitate high resolution separation for a broad range of proteins and DNA molecules. It would also be desirable that the same separation medium be capable of suppressing electroosmotic flow and reducing analyte-wall interactions, so that no capillary coating would be required. The present invention is directed to these and other goals.

SUMMARY OF THE INVENTION

The present invention concerns improved methods and compositions for conducting capillary electrophoresis (CE) to separate molecules on the basis of their respective size or charge.

In detail, the invention concerns an aqueous gel medium for facilitating the electrophoretic separation of analytes present in a sample, the medium comprising:
  (A) a non-crosslinked hydrophilic polymer;
  (B) tris(hydroxymethyl)aminomethane—borate buffer;
  (C) sodium dodecyl sulfate; and
  (D) an organic additive;

wherein the tris(hydroxymethyl)aminomethane—borate buffer has a pH above 8.0 and below 8.3, and wherein the aqueous gel medium facilitates the electrophoretic separation of the analytes by comprising a molecular sieve.

The invention further concerns the embodiment of such aqueous gel medium wherein the gel medium additionally contains one or more reagent(s) that function to help keep protein analytes in a reduced form, and especially wherein such one or more reagent(s) include a reducing reagent (especially one selected from the group consisting of 2-mercaptoethanol, dithiothreitol (DTT), dithioerythreitol (DTE), and tris(2-carboxyethyl)phosphine) and/or a metal ion chelator (especially ethylenediaminetetraacetic acid (EDTA)).

The invention further concerns the embodiment of such aqueous gel medium wherein the non-crosslinked hydrophilic polymer is selected from the group consisting of: dextran, polyacrylamide, cellulose derivatives and polyethylene oxide. The invention further concerns the embodiment of such aqueous gel medium wherein the non-crosslinked hydrophilic polymer is dextran (especially dextran having a molecular weight of 2,000 kilodaltons and possessing a non-cross-linked structure composed of approximately 95% alpha-D-(1-6) linkages).

The invention further concerns the embodiment of such aqueous gel medium wherein the organic additive is an alcohol (especially an alcohol selected from the group consisting of: methanol, ethanol, ethylene glycol and glycerol). The invention further concerns the embodiment of such aqueous gel medium wherein such alcohol is present at a concentration of from about 0.1% to about 30% (V/V)).

The invention further concerns the embodiment of such aqueous gel medium wherein the Tris-borate buffer is present at a concentration of from about 0.1M to about 1.0M, and/or wherein the aqueous gel medium has a pH of 8.1±0.1.

The invention further concerns the embodiment of such aqueous gel medium wherein the analytes include analytes selected from the group consisting of: proteins, polypeptides, peptides and nucleic acid molecules.

The invention also concerns a capillary electrophoresis system comprising a capillary tube containing an aqueous gel medium, the medium comprising:
(A) a non-crosslinked hydrophilic polymer;
(B) tris(hydroxymethyl)aminomethane—borate buffer;
(C) sodium dodecyl sulfate; and
(D) an organic additive;

wherein the tris(hydroxymethyl)aminomethane—borate buffer has a pH above 8.0 and below 8.3, and wherein the aqueous gel medium facilitates the electrophoretic separation of the analytes by comprising a molecular sieve.

The invention further concerns the embodiment of such capillary electrophoresis system wherein the gel medium additionally contains one or more reagent(s) that function to help keep protein analytes in a reduced form, and especially wherein such one or more reagent(s) include a reducing reagent (especially one selected from the group consisting of 2-mercaptoethanol, dithiothreitol (DTT), dithioerythreitol (DTE), and tris(2-carboxyethyl)phosphine) and/or a metal ion chelator (especially ethylenediaminetetraacetic acid (EDTA)).

The invention further concerns the embodiment of such capillary electrophoresis system wherein the non-crosslinked hydrophilic polymer is selected from the group consisting of: dextran, polyacrylamide, cellulose derivatives and polyethylene oxide. The invention further concerns the embodiment of such aqueous gel medium wherein the non-crosslinked hydrophilic polymer is dextran (especially dextran having a molecular weight of 2,000 kilodaltons and possessing a non-cross-linked structure composed of approximately 95% alpha-D-(1-6) linkages).

The invention further concerns the embodiment of such capillary electrophoresis system wherein the organic additive is an alcohol (especially an alcohol selected from the group consisting of: methanol, ethanol, ethylene glycol and glycerol). The invention further concerns the embodiment of such aqueous gel medium wherein such alcohol is present at a concentration of from about 0.1% to about 30% (V/V)).

The invention further concerns the embodiments of such capillary electrophoresis system wherein the Tris-borate buffer is present at a concentration of from about 0.1M to about 1.0M, and/or wherein the aqueous gel medium has a pH of 8.1±0.1.

The invention further concerns the embodiments of such capillary electrophoresis system wherein the analytes include analytes selected from the group consisting of: proteins, polypeptides, peptides and nucleic acid molecules.

BRIEF DESCRIPTION OF THE FIGURES

FIG. 2 illustrates the separation of reduced antibody (IgG) using Dextran gel matrices in different buffer system.

FIG. 3 compares the separation of protein size standards (range from 14 k to 200 k) on dextran gels with and without a glycerol additive. Legend: 1. Lysozyme; 2. Trypsin; 3. Carbonic anhydrase; 4. Ovalbumin; 5. Serum albumin; 6. Phosphorylase B; 7. β-Galactosidase; 8. Myosin.

FIG. 4 demonstrates the improvement on resolution of reduced form IgG using LPA gels in the presence of 15% glycerol organic additive.

FIG. 5 demonstrates the results of a comparison of the ability of a polyethylene oxide gel/Tris-CHES buffer system and of a 10% glycerol-containing gel capillary electrophoresis separation media of the present invention to separate IgG molecules FIG. 6 demonstrates the results of a comparison of the ability of a polyethylene oxide gel/Tris-CHES buffer system and of a 10% glycerol-containing gel capillary electrophoresis separation media of the present invention to separate a broad range of proteins.

FIG. 7 shows the separation of MW size standards with an SDS gel prepared from a new lot of Dextran polymer.

FIG. 8 shows the separation of a reduced IgG sample with an SDS gel prepared from a new lot of Dextran polymer.

FIG. 9 shows the separation of MW size standards with an SDS gel containing 1 mM DTT.

FIG. 10 shows the separation of a reduced IgG sample with an SDS gel containing 1 mM DTT.

FIG. 11 shows the separation of MW size standards with an SDS gel containing 5 mM EDTA.

FIG. 12 shows shows the separation of a reduced IgG sample with an SDS gel containing 5 mM EDTA.

DESCRIPTION OF THE PREFERRED EMBODIMENTS

Figure 1:
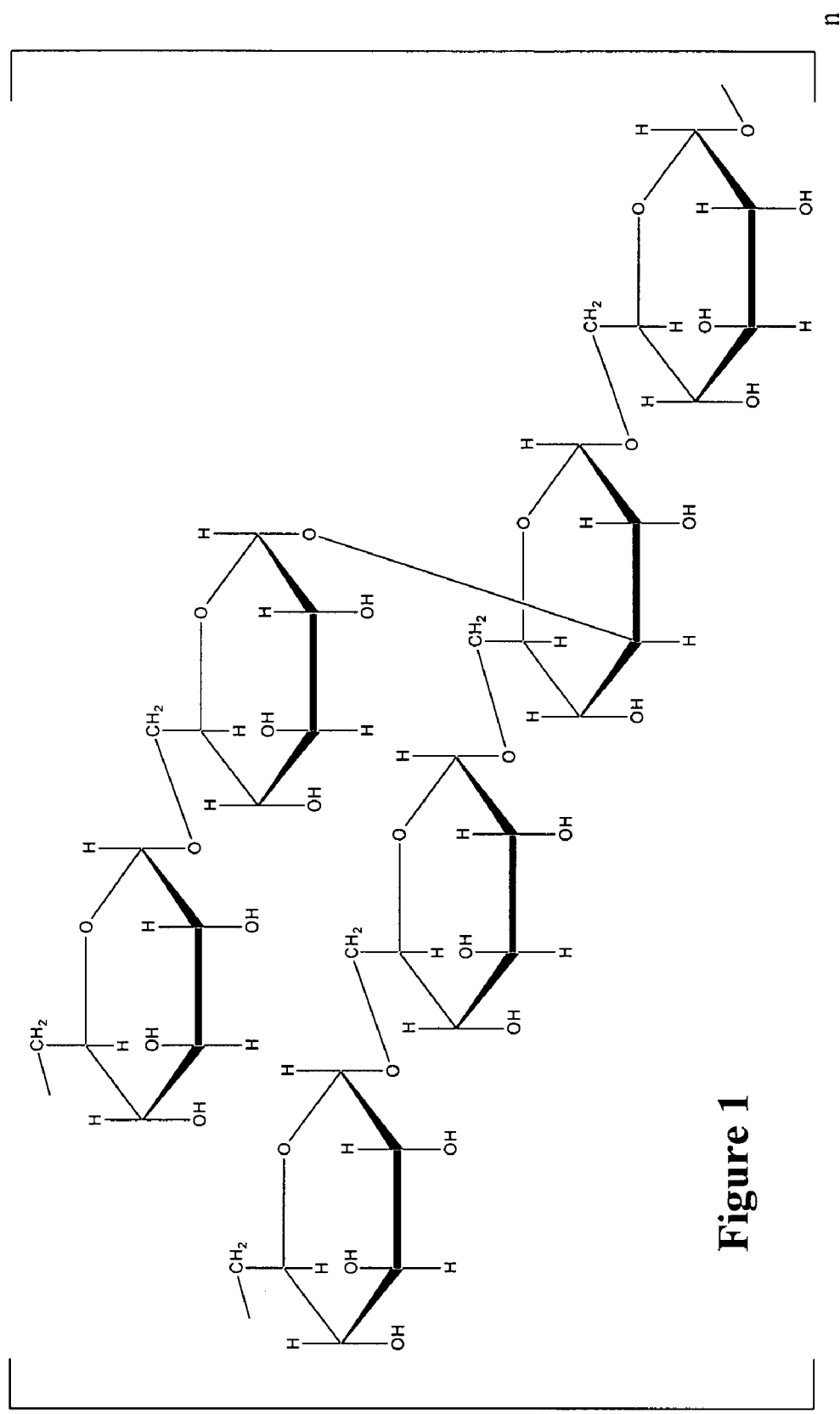
FIG. 1 shows the structure of a dextran composition.

The present invention concerns improved methods and compositions for conducting Capillary Electrophoresis (CE) to separate molecules on the basis of their respective size or charge. This invention relates to the use of hydrophilic polymers in a high concentration tris-borate buffer to suppress electroosmotic flow and to reduce analyte-wall interactions in capillary electrophoresis.

In a preferred embodiment, the invention uses one or more hydrophilic polymers, a Tris-borate buffer (pH=8.1), and organic additives to provide a separation medium capable of providing high resolution capillary electrophoresis of proteins and DNA. An unexpected enhancement of resolution is attained when conducting the electrophoresis at pH=8.1 rather than pH=8.3.

Any of a variety of hydrophilic polymers may be employed in accordance with the present invention, especially dextran, polyacrylamide, cellulose derivatives and polyethylene oxide. In highly preferred embodiments, dextran is employed, either alone or with other polymers. The dextran composition preferably possesses an average molecular weight of 2,000 kilodaltons and possesses a non-cross-linked structure composed of approximately 95% alpha-D-(1-6) linkages (see FIG. 1). The dextran does not bind to silica. Indeed, numerous reports establish that coatings are required in order to mitigate the undesired electroendosmotic flow resulting from the failure of dextran to bind silica (See, e.g., Karger, B. L. et al. U.S. Pat. No. 5,665,216; Bean, S. R. et al. (1999) "SODIUM DODECYL SULFATE CAPILLARY ELECTROPHORESIS OF WHEAT PROTEINS. 1. UNCOATED CAPILLARIES," J. Agric. Food Chem 47(10):4246-55; Zhang, Y. et al. (1996) "SEPARATION OF MYOGLOBIN MOLECULAR MASS MARKERS USING NON-GEL SIEVING CAPILLARY ELECTROPHORESIS," J. Chromatog. A 744:249-257).

In preferred embodiments, the concentration of the Tris-borate buffer is between about 0.1M to about 1.0 M. The use of the high concentration Tris-borate buffer improves the capillary surface, suppresses electroosmotic flow, and thus improves the separation capabilities of the medium.

Preferably, the organic additives employed by the present invention are alcohols (especially methanol, ethanol, ethylene glycol and glycerol) especially at concentrations of from about 0.1% to about 30%. The inclusion of the organic additives significantly improves the resolution of large proteins.

The present invention is directed to the use of the above-described aqueous gel polymer compositions to act as a molecular sieve. As used herein, the term "sieve" is intended to refer to a process of molecular separation in which molecules larger than a certain size (the "sieve size") become trapped in the sieve, which then prevents their further migration. Thus, the migration of such molecules is blocked, not merely retarded, by the methods and compositions of the present invention.

As used herein, the term "gel" is intended to refer to a system of at least two components, in which one component provides a sufficient structural framework for rigidity and other component(s) fill(s) the space between the structural units or spaces (see, The Encyclopedia of Chemistry, 4$^{th}$ Edition (Considine et al., Van Nostrum Reinhold, New York (1984), page 272). The term "gel" is often used to refer only to cross-linked polymers, rather than linear or branched polymers (such as dextrans) involving entangled monomers (see, e.g., http://neo.pharm.hiroshima-u.ac.jp/ccab/2nd/mini_review/mr130/dolnik.html; http://www.poco.phy.cam.ac.uk/teaching/A_Donald/Gels_and$_{13}$ Network.htm; Hjerten, S. et al. (1989) "HIGH-PERFORMANCE ELECTROPHORESIS OF ACIDIC AND BASIC LOW-MOLECULAR-WEIGHT COMPOUNDS AND PROTEINS IN THE PRESENCE OF POLYMERS AND NEUTRAL SURFACTANTS," J. LIQUID CHROMATOG. 12: 2471-2499), however, non-crosslinked dextran and polyacrylamide matrices used in capillary electrophoresis have nevertheless also been considered to be "gels" (see, e.g., Kemp, G. (1998) "CAPILLARY ELECTROPHORESIS: A VERSATILE FAMILY OF ANALYTICAL TECHNIQUES," Biotechnol. Appl. Biochem. 27:9-17; Wu, D. et al. (1992) ("SODIUM DODECYL SULFATE-CAPILLARY GEL ELECTROPHORESIS OF PROTEINS USING NON-CROSS-LINKED POLYACRYLAMIDE," J. Chromatogr. 608:349-356). The gels of the present invention may be composed of either cross-linked or non-crosslinked polymers. Two gel matrix compositions (SDS "Gel A" and SDS "Gel B") are of particular interest. Their compositions are described below:

Compositions of Preferred Embodiments of the Invention

| Component | SDS "Gel A" | SDS "Gel B" |
|---|---|---|
| Dextran (MW 2,000,000) Matrix | 9% (w/v) | 10% (w/v) |
| Tris(hydroxymethyl)aminomethane | 0.6 M | 0.6 M |
| Boric Acid (pH = 8.1) ± 0.10 (at 25° C. ± 1.5° C.) | 0.6 M | 0.6 M |
| Sodium Dodecyl Sulfate (SDS) | 0.1% (w/v) | 0.1% (w/v) |
| Glycerol | — | 10% |

The performance of SDS Gel A and SDS gel B with protein analytes can be further improved by the inclusion of one or more reagent(s) that function to help keep the protein analytes in a reduced form. In one embodiment, such reagents comprise reducing reagent(s) (e.g., 2-mercaptoethanol, dithiothreitol (DTT), dithioerythritol (DTE), tris(2-carboxyethyl)phosphine, etc.). Dithiothreitol (DTT) is particularly preferred for this purpose. The concentration of such reducing reagent(s) in the gel will preferably be from about 0.1 mM to about 15 mM, and more preferably from about 0.5 mM to about 5 mM. 1 mM DTT is particularly preferred.

Such reagents can additionally or alternatively comprise reagents that prevent or reduce protein oxidation. Generally, protein oxidation is catalyzed by heavy metal ions. Thus, metal ion chelators or sequesters can be provided so as to complex with such metal ions and prevent or reduce protein oxidation. Ethylene diamine tetraacetic acid (EDTA) is particularly preferred. The concentration of such reducing reagent(s) in the gel will preferably be from about 0.1 mM to about 15 mM, and more preferably from about 2 mM to about 10 mM. 5 mM EDTA is particularly preferred.

Preferred Composition of the Invention

| Component | Concentration |
|---|---|
| Dextran (MW 2,000,000) Matrix | 10% (w/v) |
| Tris(hydroxymethyl)aminomethane | 0.6 M |
| Boric Acid (pH = 8.1) ± 0.10 (at 25° C. ± 1.5° C.) | 0.6 M |
| Sodium Dodecyl Sulfate (SDS) | 0.2% (w/v) |
| Glycerol | 10% |
| EDTA | 5 mM |

Both reducing reagents and reagents that prevent or reduce protein oxidation can be used in the same composition, if desired, although the performance is slightly better than only one class reagent (e.g., adding only EDTA or DTT, but not both). Since DTT is partially unstable upon storage, EDTA is the preferred reagent to help keep the protein analytes in a reduced form. The major improvement obtained through the inclusion of DTT or EDTA is the elimination of protein oxidation during CE separation, and therefore the improvement in separation efficiency.

A preferred method for preparing the compositions of the present invention comprises the steps of:

(a) Preparing tris-borate buffer;
(b) Adding organic additives into the buffer;
(c) Preparing the gel matrix by mixing the polymer completely into buffer solution; and
(d) Performing the separation using a capillary electrophoresis instrument.

The compositions and methods of the present invention may be used to separate biomolecules (such as polysaccharides, proteins, polypeptides, peptides, nucleic acid molecules (DNA, RNA, etc.)) while suppressing electroosmotic field and avoiding the wall-adsorption of silica capillaries for other CE applications. The compositions and methods of the present invention may be used on microfluidic or microfabricated devices for protein and DNA and other biomolecular separations.

The compositions and methods of the present invention are particularly suitable for use in automated or semi-automated capillary electrophoretic systems (for example in concert with the teachings of U.S. Pat. Nos. 6,001,230; 5,320,730, etc.). A particularly preferred such electrophoretic system includes a P/ACE MDQ (Beckman-Coulter) configured with a selectable-wavelength UV/V is (for example, 200, 214, 254 and 280 nm) detector, UV source optics, a dual-wavelength laser-induced fluorescence detector, a 488 nm argon ion laser module, a temperature-controlled sample storage module, and 32 Karat™ Software (Beckman-Coulter) configured on an IBM personal computer.

The compositions and methods of the present invention may be employed in concert with assay procedures (e.g., immunoassays, etc.; see U.S. Pat. No. 5,863,401) to permit the simultaneous analysis of multiple analytes. Likewise, the compositions and methods of the present invention may be employed for quantitating the concentration of protein components and of the total protein in fluids (see, U.S. Pat. No. 5,490,909).

The compositions and methods of the present invention provide salient advantages over prior capillary electrophoretic systems. These advantages include: (1) better resolution; (2) no requirement for capillary coating; (3) easier to manufacture; (4) lower cost due to inexpensive materials and minimum labor; (5) no toxic chemical solvents involved.

Having now generally described the invention, the same will be more readily understood through reference to the following examples, which are provided by way of illustration, and are not intended to be limiting of the present invention, unless specified.

EXAMPLE 1

Preparation of Capillary Electrophoresis Separation Media "SDS Gel A"

"SDS Gel A" is prepared as follows:

Raw materials and equipment:

| | |
|---|---|
| Dextran, MW 2,000,000 (Sigma, D5376) | 9% |
| Tris(hydroxymethyl)aminomethane ("Tris") (Sigma, T-1503) | 0.6 M |
| Boric Acid (Sigma, B-0394) | 0.6 M |
| Sodium dodecyl sulfate ("SDS") (ICN Biomedicals Inc., 811034) | |
| 2 liter reaction flask with 3 necks | |
| Balance | |
| Mechanical stirring apparatus | |
| pH meter | |
| Teflon stirring bars | |
| Filter (0.2 μm (Nalgene, Cat. No. 150-0020) | |
| 1. Preparation of 0.6 M tris-borate buffer (1 L Batch) 72.66 g Tris 37.10 g Boric Acid 1 liter of de-ionized water pH = 8.1 ± 0.10 (at 25° C. ± 1.5° C.) Filter the buffer with 0.2 μm filter system. | |
| 2. Gel buffer preparation Add 1 g SDS to 1 liter tris-borate buffer solution. Start stirring. After SDS powder is completely dissolved, slowly add 90 g Dextran to the buffer while stirring. Continue stirring at room temperature for 18 to 24 hr. | |

Store the gel buffer in a clean container at room temperature.

EXAMPLE 2

Preparation of Capillary Electrophoresis Separation Media "SDS Gel B"

"SDS Gel B" is prepared as follows:

Raw materials and equipment:

| | |
|---|---|
| Dextran, MW 2,000,000 (Sigma, D5376) | 10% |
| Tris(hydroxymethyl)aminomethane ("Tris") (Sigma, T-1503) | 0.6 M |
| Boric Acid (Sigma, B-0394) | 0.6 M |
| Sodium dodecyl sulfate ("SDS") (ICN Biomedicals Inc., 811034) Glycerol (Sigma, G7893) | 10% |
| 2 liter reaction flask with 3 necks | |
| Balance | |
| Mechanical stirring apparatus | |
| pH meter | |
| Teflon stirring bars | |
| Filter (0.2 μm (Nalgene, Cat. No. 150-0020) | |
| 1. Preparation of 0.6 M tris-borate glycerol buffer (1 L Batch) 72.66 g Tris 37.10 g Boric Acid 900 ml of de-ionized water pH = 8.1 ± 0.10 (at 25° C. ± 1.5° C.). Add 100 ml glycerol into buffer, and stir for 10 minutes. Filter the buffer with 0.2 μm filter system. | |
| 2. Gel buffer preparation Add 1 g SDS to 1 liter tris-borate glycerol buffer solution. Start stirring. After SDS powder is completely dissolved, slowly add 90 g Dextran to the buffer while stirring. Continue stirring at room temperature for 18 to 24 hr. | |

Store the gel buffer in a clean container at room temperature.

EXAMPLE 3

SDS Sample Buffer

"SDS Sample Buffer" is prepared as follows:

Raw materials and equipment:
Trizma® Base (Sigma, T-1503)
Trizma® hydrochloride (Sigma T3253)
Sodium dodecyl sulfate ("SDS") (ICN Biomedicals Inc., 811034)
2 liter reaction flask with 3 necks
Balance
Mechanical stirring apparatus
pH meter Teflon stirring bars
Filter (0.2 μm (Nalgene, Cat. No. 150-0020)
1. Preparation of SDS Sample Buffer (1 L Batch)
   10.94 g Trizma® Base
   1.52 g Trizmag hydrochloride
   1 liter of de-ionized water
   Add 10 g SDS powder into buffer and stir to dissolve. Filter the buffer with 0.2 μm filter system.

EXAMPLE 4

Gel Capillary Electrophoresis Separation Media

Many hydrophilic polymers, such as dextran, polyacrylamide, and cellulose-derivatives bind poorly onto capillary surface, and therefore coated capillaries are generally used with gel matrix containing those polymers. However, when such polymers are dissolved into high concentration tris-borate buffer, in accordance with the principles of the present invention, the separation medium can dynamically coat the capillary surface. As a result, the electroosmotic flow is suppressed and analyte-surface interaction is reduced. FIG. 2 illustrates the separation of reduced antibody (IgG) using dextran gel matrices in different buffer systems. For dextran gel in Tris-Taps and Tris-HCl buffers, no peak is detected in 60 min., indicating the existence of strong electroosmotic flow. In contrast, the use of a dextran gel matrix with a Tris-borate buffer, effectively suppresses electroosmotic flow, and all the heavy chain, light chain, and glycosylated components are well separated.

It is also found that resolution of large proteins is significantly improved through the addition of organic additives, including ethylene glycol and glycerol. FIG. 3 compares the separation of protein size standards (range from 14 k to 200 k) on dextran gels with or without a glycerol organic additive. As shown in FIG. 3, the addition of 10% glycerol to the dextran gel significantly improves the resolution of a broad range proteins.

FIG. 4 demonstrates the improvement on resolution of reduced form IgG using LPA gels in the presence of 15% glycerol organic additive. The glycosylated heavy chain is found to be well separated from the non-glycosylated heavy chain in LPA in the presence of 15% glycerol organic additive, while no separation is observed in the LPA gel lacking glycerol.

EXAMPLE 5

Comparison of Gel Capillary Electrophoresis Separation Media With Polyethylene Oxide/Tris-CHES Buffer Separation Medium The ability of the gel capillary electrophoresis separation media of the present invention (containing 10% glycerol) to separate proteins is compared with that of a polyethylene oxide gel/Tris-CHES buffer system (Beckman-Coulter).

Compared to the polyethylene oxide gel/Tris-CHES buffer system, the gel capillary electrophoresis separation media of the present invention containing 10% glycerol is found to offer significantly better resolution for separation of IgG (FIG. 5) and a broad range of proteins (FIG. 6). The glycosylated heavy chain is baseline resolved from the non-glycosylated heavy chain in the dextran-based gel, whereas no separation is observed with the polyethylene oxide gel/Tris-CHES buffer system (Beckman-Coulter).

EXAMPLE 6

Comparison of Gel Capillary Electrophoresis Separation Media with Media Containing Reagent(s) That Function To Help Keep Protein Analytes in a Reduced Form The original gel formulation exhibited inconsistencies of performance with respect to protein analytes, especially when different lot of raw materials were used. To further improve on gel performance, regents that function to help keep protein analytes in a reduced form were added to the gel formulation. The performance of the above-described dextran gels with respect to protein analytes is found to be improved by the inclusion of one or more of such reagent(s).

In order to demonstrate such improvement, tris-borate gels are prepared having EDTA or DTT, and their performance relative to gels lacking these reagents is assessed. FIGS. 7 and 8 show the performance of such dextran-SDS gels (prepared from a new lot of Dextran polymer) with respect to the separation of molecular weight (MW) size standards or of a reduced IgG sample. As seen in FIG. 7, the 50 kD protein exhibits a very broad peak due to partially oxidation during separation. A seen in FIG. 8, the gel profile exhibits very broad peaks and poor resolution. In addition, a broad peak for heavy-heavy chain interactions is observed. This is believed to be due to partial oxidation of the proteins (e.g., the reformation of a disulfide bond between or within the same protein molecule (such as between or within the same heavy chain IgG molecule) during separation. For example, a broad heavy-heavy chain peak is observed during separation of reduced IgG, indicating reformation of disulfide bond between two heavy chain (FIG. 8).

In contrast to such results, FIG. 9 and FIG. 10 show the improved resolution obtainable, with respect to the MW size standards, and the reduced IgG sample, respectively, when 1 mM DTT is included in the gel. A very sharp peak of 50 kD protein is obtained after adding DTT into the gel (FIG. 9). The separation of IgG reduced sample is also significantly improved (FIG. 10).

FIG. 11 and FIG. 12 show the improved resolution obtainable, with respect to the MW size standards, and the reduced IgG sample, respectively, when 5 mM EDTA is included in the gel. The separation is significantly improved. Since the partial oxidation is substantially or completely eliminated, all proteins peaks are very sharp.

All publications and patents mentioned in this specification are herein incorporated by reference to the same extent as if each individual publication or patent application was specifically and individually indicated to be incorporated by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An aqueous gel separation medium having a structural framework to facilitate the separation of introduced analytes, wherein said aqueous gel separation medium consists essentially of components:

(A) an aqueous tris(hydroxymethyl)aminomethane—borate buffer solution having a pH above 8.0 and below 8.3;
(B) sodium dodecyl sulfate;
(C) an alcohol;
(D) one or more reagent(s) that function to help keep introduced analytes in a reduced form; and
(E) a hydrophilic polymer dissolved in said components (A)-(D), wherein said dissolved hydrophilic polymer provides said gel separation medium's structural framework.

2. The aqueous gel separation medium of claim 1, wherein said one or more reagent(s) include a reducing reagent.

3. The aqueous gel separation medium of claim 2, wherein said reducing reagent is selected from the group consisting of: 2-mercaptoethanol, dithiothreitol (DTT), dithioerythreitol (DTE), and tris(2-carboxyethyl)phosphine.

4. The aqueous gel separation medium of claim 3, wherein said reducing reagent is dithiothreitol (DTT).

5. The aqueous gel separation medium of claim 1, wherein said one or more reagent(s) include a metal ion chelator.

6. The aqueous gel separation medium of claim 5, wherein said metal ion chelator is ethylenediaminetetraacetic acid (EDTA).

7. The aqueous gel separation medium of claim 1, wherein said hydrophilic polymer is selected from the group consisting of: dextran, polyacrylamide, cellulose derivatives and polyethylene oxide.

8. The aqueous gel separation medium of claim 7, wherein said hydrophilic polymer is dextran.

9. The aqueous gel separation medium of claim 8, wherein said dextran has a molecular weight of 2,000 kilodaltons and possesses a structure composed of approximately 95% alpha-D-(1-6) linkages.

10. The aqueous gel separation medium of claim 1, wherein said alcohol is present at a concentration of from about 0.1% to about 30% (V/V).

11. The aqueous gel separation medium of claim 10, wherein said alcohol is selected from the group consisting of: methanol, ethanol, ethylene glycol and glycerol.

12. The aqueous gel separation medium of claim 11, wherein said alcohol is glycerol.

13. The aqueous gel separation medium of claim 12, wherein said glycerol is present at a concentration of from about 0.1% to about 30% (V/V).

14. The aqueous gel separation medium of claim 1, wherein said Tris-borate buffer is present at a concentration of from about 0.1M to about 1.0M.

15. The aqueous gel separation medium of claim 1, wherein said aqueous gel separation medium has a pH of 8.1±0.1.

16. The aqueous gel separation medium of claim 1, wherein said introduced analytes include analytes selected from the group consisting of: proteins, polypeptides, peptides and nucleic acid molecules.

17. A capillary electrophoresis system comprising a capillary tube containing an aqueous gel separation medium having a structural framework to facilitate the separation of introduced analytes, wherein said aqueous gel separation medium consists essentially of components:
(A) an aqueous tris(hydroxymethyl)aminomethane—borate buffer solution having a pH above 8.0 and below 8.3;
(B) sodium dodecyl sulfate;
(C) an alcohol;
(D) one or more reagent(s) that function to help keep introduced analytes in a reduced form; and
(E) a hydrophilic polymer dissolved in said components (A)-(D), wherein said dissolved hydrophilic polymer provides said gel separation medium's structural framework.

18. The capillary electrophoresis system of claim 17, wherein said one or more reagent(s) that function to help keep analytes in a reduced form include a reducing reagent.

19. The capillary electrophoresis system of claim 18, wherein said reducing reagent is selected from the group consisting of: 2-mercaptoethanol, dithiothreitol (DTT), dithioerythreitol (DTE), and tris(2-carboxyethyl)phosphine.

20. The capillary electrophoresis system of claim 19, wherein said reducing reagent is dithiothreitol (DTT).

21. The capillary electrophoresis system of claim 17, wherein said one or more reagent(s) include a metal ion chelator.

22. The capillary electrophoresis system of claim 21, wherein said metal ion chelator is ethylenediaminetetraacetic acid (EDTA).

23. The capillary electrophoresis system of claim 17, wherein said hydrophilic polymer is selected from the group consisting of: dextran, polyacrylamide, cellulose derivatives and polyethylene oxide.

24. The capillary electrophoresis system of claim 23, wherein said hydrophilic polymer is dextran.

25. The capillary electrophoresis system of claim 24, wherein said dextran has a molecular weight of 2,000 kilodaltons and possesses a structure composed of approximately 95% alpha-D-(1-6) linkages.

26. The capillary electrophoresis system of claim 17, wherein said alcohol is present at a concentration of from about 0.1% to about 30% (V/V).

27. The capillary electrophoresis system of claim 26, wherein said alcohol is selected from the group consisting of: methanol, ethanol, ethylene glycol and glycerol.

28. The capillary electrophoresis system of claim 27, wherein said alcohol is glycerol.

29. The capillary electrophoresis system of claim 28, wherein said glycerol is present at a concentration of from about 0.1% to about 30% (V/V).

30. The capillary electrophoresis system of claim 17, wherein said Tris-borate buffer is present at a concentration of from about 0.1M to about 1.0M.

31. The capillary electrophoresis system of claim 17, wherein said aqueous gel separation medium has a pH of 8.1±0.1.

32. The capillary electrophoresis system of claim 17, wherein said introduced analytes include analytes selected from the group consisting of: proteins, polypeptides, peptides, polysaccharides, and nucleic acid molecules.

33. A capillary electrophoresis system comprising a capillary tube, wherein said capillary tube has an uncoated inner surface, and contains an aqueous gel separation medium, having a structural framework to facilitate the separation of introduced analytes, wherein said aqueous gel separation medium comprises components:
(A) an aqueous tris(hydroxymethyl)aminomethane—borate buffer solution having a pH above 8.0 and below 8.3;
(B) sodium dodecyl sulfate;
(C) an alcohol;
(D) one or more reagent(s) that function to help keep introduced analytes in a reduced form; and
(E) a hydrophilic polymer dissolved in said components (A)-(D), wherein molecules of said hydrophilic wherein said dissolved hydrophilic polymer provides said gel separation medium's structural framework.

and wherein said gel separation medium forms a dynamic coating on said uncoated inner surface of said capillary tube.

34. The capillary electrophoresis system of claim 33, wherein said one or more reagent(s) that function to help keep analytes in a reduced form include a reducing reagent.

35. The capillary electrophoresis system of claim 34, wherein said reducing reagent is selected from the group consisting of: 2-mercaptoethanol, dithiothreitol (DTT), dithioerythreitol (DTE), and tris(2-carboxyethyl)phosphine.

36. The capillary electrophoresis system of claim 35, wherein said reducing reagent is dithiothreitol (DTT).

37. The capillary electrophoresis system of claim 33, wherein said one or more reagent(s) include a metal ion chelator.

38. The capillary electrophoresis system of claim 37, wherein said metal ion chelator is ethylenediaminetetraacetic acid (EDTA).

39. The capillary electrophoresis system of claim 33, wherein said hydrophilic polymer is selected from the group consisting of: dextran, polyacrylamide, cellulose derivatives and polyethylene oxide.

40. The capillary electrophoresis system of claim 39, wherein said hydrophilic polymer is dextran.

41. The capillary electrophoresis system of claim 40, wherein said dextran has a molecular weight of 2,000 kilodaltons and possesses a structure composed of approximately 95% alpha-D-(1-6) linkages.

42. The capillary electrophoresis system of claim 33, wherein said alcohol is present at a concentration of from about 0.1% to about 30% (V/V).

43. The capillary electrophoresis system of claim 42, wherein said alcohol is selected from the group consisting of: methanol, ethanol, ethylene glycol and glycerol.

44. The capillary electrophoresis system of claim 43, wherein said alcohol is glycerol.

45. The capillary electrophoresis system of claim 44, wherein said glycerol is present at a concentration of from about 0.1% to about 30% (V/V).

46. The capillary electrophoresis system of claim 33, wherein said Tris-borate buffer is present at a concentration of from about 0.1M to about 1.0M.

47. The capillary electrophoresis system of claim 33, wherein said aqueous gel separation medium has a pH of 8.1±0.1.

48. The capillary electrophoresis system of claim 33, wherein said introduced analytes include analytes selected from the group consisting of: proteins, polypeptides, peptides, polysaccharides, and nucleic acid molecules.

* * * * *